(12) United States Patent
Gimble et al.

(10) Patent No.: US 6,555,374 B1
(45) Date of Patent: Apr. 29, 2003

(54) MULTIPLE MESODERMAL LINEAGE DIFFERENTIATION POTENTIALS FOR ADIPOSE TISSUE-DERIVED STROMAL CELLS AND USES THEREOF

(75) Inventors: Jeffrey Martin Gimble, Chapel Hill, NC (US); Juan-Di Chang Halvorsen, Holly Springs, NC (US); William O. Wilkison, Bahama, NC (US)

(73) Assignee: Artecel Sciences, Inc., Durham, NC (US)

( * ) Notice: Subject to any disclaimer, the term of this patent is extended or adjusted under 35 U.S.C. 154(b) by 118 days.

(21) Appl. No.: 09/638,544

(22) Filed: Aug. 14, 2000

Related U.S. Application Data
(60) Provisional application No. 60/149,849, filed on Aug. 19, 1999.

(51) Int. Cl.[7] .................................................. C12N 5/08
(52) U.S. Cl. ...................................... 435/371; 435/372
(58) Field of Search ................................. 435/366, 370, 435/371, 372

(56) References Cited

U.S. PATENT DOCUMENTS

| | | | |
|---|---|---|---|
| 5,486,359 A | | 1/1996 | Caplan et al. |
| 5,580,781 A | * | 12/1996 | Naughton et al. |
| 5,599,703 A | * | 2/1997 | Davis et al. |
| 5,736,396 A | | 4/1998 | Bruder et al. |
| 5,763,266 A | * | 6/1998 | Palsson et al. |
| 5,811,094 A | | 9/1998 | Caplan et al. |
| 5,827,735 A | | 10/1998 | Young et al. |
| 5,863,531 A | | 1/1999 | Naughton et al. |
| 5,879,940 A | | 3/1999 | Torok-Storb et al. |
| 5,902,741 A | | 5/1999 | Purchio et al. |
| 5,908,784 A | | 6/1999 | Johnstone et al. |
| 5,942,225 A | | 8/1999 | Bruder et al. |
| 6,030,836 A | | 2/2000 | Thiede et al. |
| 6,103,522 A | | 8/2000 | Torok-Storb et al. |
| 6,153,432 A | | 11/2000 | Halvorsen et al. |
| 6,200,606 B1 | | 3/2001 | Peterson et al. |
| 6,242,200 B1 | | 6/2001 | Wilkison et al. |
| 6,316,247 B1 | | 11/2001 | Katz et al. |

FOREIGN PATENT DOCUMENTS

| | | |
|---|---|---|
| WO | WO96/02662 A1 | 1/1996 |
| WO | WO98/20731 A1 | 5/1998 |
| WO | WO99/43286 A1 | 2/1999 |
| WO | WO99/61587 A1 | 2/1999 |
| WO | WO00/53795 A1 | 9/2000 |
| WO | WO00/06232 A1 | 10/2000 |

OTHER PUBLICATIONS

Burris et al., A Novel Method for Analysis of Nuclear Receptor Function at Natural Promoters: Peroxisome Proliferator–Activated Receptor γ Agonist Actions on a P2 Gene Expression Detected Using Branched DNA Messenger RNA Quantitation, *Molecular Endocrinology*, 1999, 13, 3, 410.

Gimble, Jeffrey Martin, The Function of Adipocytes in the Bone Marrow Stroma, *The New Biologist*, 1990, 2, 4, 304.
Gimble et al., Nuclear Hormone Receptors and Adipogenesis, *Critical Reviews in Eukaryotic Gene Expression*, 1998, 8(2), 141.
Gimble et al., Adipocyte Biology of the Bone, *Adipocyte Biology and Hormone Signaling*, IOS Press, The Netherlands, 2000, 231.
Mizuno, M.D., Hiroshi, The Myogenic Potential of Human Processed Lipoaspirates—Part I: Morphological, immunohistochemical analysis and gene expression, *J. Jpn.P.R.S.*, 2001, 21, 427.
Mizuno et al., Myogenic Differentiation by Human Processed Lipoaspirate Cells, *Plastic and Reconstructive Surgery* 2002, 109, 1, 199.
Saladin et al., Differential Regulation of Peroxisome Proliferator Activated Receptor γ1 (PPARγ1) and PPARγ2 Messenger RNA Expression in the Early Stages of Adipogenesis[1], *Cell Growth & Differentiation*, 1999, 10, 43.
Zuk et al., Multilineage Cells from Human Adipose Tissue: Implications for Cell–Based Therapies, *Tissue Engineering*, 2001, 7, 2, 211.
U.S. patent application Ser. No. 60/123,711, Katz et al., filed Mar. 10, 1999.
U.S. patent application Ser. No. 60/163,462, Katz et al., filed Oct. 29, 1999.
Brown, J.M. et al., "Trans–10, Cis–12, but not Cis–9, Trans–11, Conjugated Linoleic Acid Attenuates Lipogenesis in Primary Cultures of Stromal Vascular Cells form Human Adipose Tissue," (2001) J Nutr. 131(9):2316–21.
Gronthos, et al., Surface Protein Characterization of Human Adipose Tissue–Derived Stromal Cells, *J. Cell. Physiol.* 189:54–63 Aug. 16, 2001.
Halvorsen, Y, et al., "Adipose–derived stromal cells– their utility and potential in bone formation," *International Journal of Obesity*, (2000) Suppl 4, S41–S44.
Halvorsen, Y, et. al., "Thiazolidinediones and Glucocorticoids Synergistically Induce Differentiation of Human Adipose Tissue Stromal Cells: Biochemical, Cellular, and Molecular Analysis," *Metabolism*, vol. 50, No. 4 (2001): pp 407–413.
Halvorsen, Y, et al., "Human adipocyte proteomics—a complementary way of looking at fat," (2000), *Pharmacogenomics*, 1(2): pp. 179–185.

(List continued on next page.)

Primary Examiner—Jon P. Weber
(74) Attorney, Agent, or Firm—King & Spalding, LLP; Sherry M. Knowles, Esq.; Joseph M. Bennett-Paris

(57) ABSTRACT

The invention relates to methods and compositions for the differentiation of stromal cells from adipose tissue into hematopoietic supporting stromal cells and myocytes of both the skeletal and smooth muscle type. The cells produced by the methods are useful in providing a source of fully differentiated and functional cells for research, transplantation and development of tissue engineering products for the treatment of human diseases and traumatic tissue injury repair.

28 Claims, 5 Drawing Sheets

OTHER PUBLICATIONS

Halvorsen, Y, et al., Extracellular Matrix Mineralization and Osteoblast Gene Expression by Human Adipose Tissue–Derived Stromal Cells, (2001) *Tissue Engineering* 7.

Harp, Joyce B., et al., "Differential Expression of Signal Transducers and Activators of Transcription during Human Adipogenesis," (2001) *Biochem. Biophys. Res, Comm.* 281, 907–912.

Sen, A. et al., "Adipogenic Potential of Human Adipose Derived Stromal Cells form Multiple Donors is Heterogeneous," (2001) *J. Cell. Biochem.* 81:312–319.

Zhou, L, et al., Analysis of the pattern of gene expression during human adipogenesis by DNA microarray, (1999) *Biotechnology Techniques* 13: 513–517.

Beresford, "Osteogenic Stem Cells and the Stromal System of Bone and Marrow," *Clin Orthop Res*, (1989), 240:270–280.

Chomczynski & Sacchi, "Single–Step Method of RNA Isolation by Acid Guanidinium Thiocyanate–Phenol–Chloroform Extraction," *Analytical Biochem*, (1987), 162:156–159.

Constantinides et al., "Functional straited muscle cells from non–myoblast precursors following 5–azacytidine treatment," *Nature*, (1977) 267:364.

Dani et al., "Differentiation of embryonic stem cells into adipocytes in vitro," *J. Cell Sci.*, (1997) 110:1279.

Dennis et al., "A Quadripotential Mesenchymal Progenitor Cell Isolated from the Marrow of an Adult Mouse," *JBMR*, (1999), 14:700–709.

Dorheim et al., "Osteoblastic Gene Expression During Adiopogensis in Hematopoietic Supporting Murine Bone Marrow Stromal Cells," *J. Cell. Physiol.*, (1993), 154:317–328.

Gimble et al., "Adipogensis in a Myeloid Supporting Bone Marrow Stromal Cell Line," *J. Cell Biochem*, (1992), 50:73–82.

Gimble et al., "Characterization of Murine Bone Marrow and Spleen–Derived Stromal Cells: Analysis of Leukocyte Marker and Growth Factor mRNA transcript Levels," *Blood*, (1989) 74:303–311.

Gimble et al., "The Function of Adipocytes in the Bone Marrow Stromal: An Update," *Bone*, (1996), 19:421–428.

Gimble et al., "Adipogensis in a murine bone marrow stromal cell line capable of supporting B lineage lymphocyte growth and proliferation: biochemical and molecular characterization," *Eur. J. Immunol.*, (1990), 20:379–386.

Hayashi et al., "The CD9 Molecule on Stromal Cells," *Leuk Lymphoma*, (2000), 38:265–270.

Haynesworth et al., "Characterization of Cells with Osteogenic Potential from Human Marrow," *Bone*, (1992), 13:81–88.

Jacobsen et al., "Highly Restricted Expression of a Stromal Cell Determinant in Mouse Bone Marrow In Vivo," *J Exp Med*, (1992), 176:927–935.

Johnson RS, "Targeting of Nonexpressed Genes in Embryonic Stem Cells Via Homologous Recombination," *Science*, (1989), 245:1234.

Jones & Taylor, *Cell*, "Cellular Differentiation, Cytidine Analogs and DNA Methylation," (1980), 20:85–92.

Kaplan, "Skin and Bones," *Arch. Dermatol.*, (1996), 132:815–818.

Kelly et al., "Murine Bone Marrow Stromally Derived BMS2 Adipocytes Support Differentiation and Function of Osteoclast–Like Cells in Vitro," *Endocrinol.*, (1998), 139:2092–2101.

Kincade et al., "CD44 and Other Cell Interaction Molecules Contributing to B Lymphopoiesis," *Curr Top Microbiol Immunol*, 184:215–222.

Kuznetsov et al., "Single–Colony Derived Strains of Human Marrow Stromal Fibroblasts From Bone After Transplantation In Vivo," *JBMR*, (1997), 12:1335–1347.

Lassar, et al., "Transfection of a DNA Locus That Mediates the Conversion of 10T1/2 Fibroblasts to Myoblasts," *Cell*, (1986), 47:649.

McCulloch et al., "Genetic Factors Affecting the Control of Hemopoiesis," *Proc. Can. Cancer Conf.*, (1996) 6:336–356.

Miyake et al., "Monoclonal Antibodies to Pgp–1CD44 Block Lympho–Hemopoiesis in Long–Term Bone Marrow Cultures," *J Exp Med*, (1990), 171:477–488.

Miyake et al., "A VCAM–like Adhesion Molecule on Murine Bone Marrow Stromal cells Mediates Binding of Lymphocyte Precursors in Culture," *J Cell Biol.*, (1991), 114:557–565.

Miyake et al., "Evidence for a Role of the Integrin VLA–4 in Lympho–hemopoiesis," *J Exp Med*, (1991), 173:599–607.

Nuttall et al., Human Trabecular Bone Cells Are Able to Express Both Osteoblastic and Adipocytic Phenotype: Implications for Osteopenic Disorders *JBMR* (1998), 13:371–382.

O'Shea KS, "Embryonic Stem Cell Models of Development," *Anat. Rec.*, (1999) 257:32.

Owen, Nuffield Department of Orthopaedic Surgery, University of Oxford, UK, "Marrow stromal stem cells," *J. Cell. Sci.*, (1988), 10:63–76 Abstract only.

Park, et al., "Interconversion Potential of Cloned Human Marrow Adipocytes In Vitro," *Bone*, (1999), 24:549–554.

Pennisi & Williams, "Will Dolly Send in the Clones?," *Science*, (1997), 275:1415–1416.

Pennisi, "Cloned Mice Provide Company for Dolly," *Science*, (1998), 281:495.

Phinney, "Plastic Adherent Stromal Cells From the Bone Marrow of Commonly Used Strains of Inbred Mice: Variations in Yield, growth, and Differentiation," *J. Cell. Biochem.*, (1999), 72:570–585.

Pietrangeli et al., "Stromal cell lines which support lumphocyte growth: characterization, sensitivity to radiation and responsiveness to growth factors," *Eur. J. Immunol.*, (1988), 18:863–872.

Pittenter et al., "Multilineage Potential of Adult Human Mesenchymal Stem Cells," *Science*, (1999), 284: 143–147.

Remoncourt et al., "Neurons derived in vitro from ES cells express homeoproteins characteristic of motoneurons and interneurons," *Mech. Dev.*, (1998) 79:185.

Remy–Martin et al., "Vascular smooth muscle differentiation of murine stroma: A sequential model," *Exp. Hematol.*, (1999), 27:1782–1795.

* cited by examiner

Table 1: Characterization of Adipose Derived Stromal Cell Surface Markers Based on Antibody and PCR Detection

| Positive Markers | Negative Markers |
| --- | --- |
| CD9 - Tetraspan Protein | CD11a |
| CD29 - Integrin $\beta_1$ | CD11 b |
| CD34 | CD11 c |
| CD44 - Hyaluronate Receptor | CD 14 |
| CD49 d, e - Integrins $\alpha_{4,5}$ | CD31 |
| CD54 - ICAM1 | CD45 |
| CD55 - Decay Accelerating Factor | CD50 - ICAM3 |
| CD56 - NCAM | HLA DR (Class II) |
| CD59 - Complement Inhibitor Protein | |
| CD105 - Endoglin | |
| CD106 - VCAM1 | |
| CD146 - Muc 18 | |
| CD 166 - ALCAM | |
| $\alpha$ Smooth Muscle Actin | |
| Collagen I | |
| Collagen III | |
| Alkaline Phosphatase | |
| HLA Class I | |

FIGURE 1A

Table 2. Cytokines Expressed by Adipose-Derived Stromal Cells Constitutively or Following Endotoxin (LPS) Induction

| |
|---|
| M-CSF-Macrophage Colony Stimulating Factor |
| G-CSF-Granulocyte Colony Stimulating Factor |
| GM-CSF-Granulocyte/Monocyte Colony Stimulating Factor |
| LIF-Leukemia Inhibitory Factor |
| SCF-Stem Cell Factor (c-kit Ligand). |
| BMP 2,4-Bone Morphogentic Proteins 2,4 |
| IL-6,7,8,11-Interleukins 6,7,8, 11 |
| Flt- 3 Ligand |

The listed cytokine mRNAs were detected by polymerase chain reaction using the following oligonucleotide primer sets:

| | | |
|---|---|---|
| M-CSF | Forward | 5' TTGGGAGTGGACACCTGCAGTCT 3' (SEQ ID NO: 9) |
| | Reverse | 5' CCTTGGTGAAGCAGCTCTTCAGCC 3' (SEQ ID NO: 10) |
| G-CSF | Forward | 5' AGCTTCCTGCTCAAGTGCTTAGAGA 3' (SEQ ID NO: 7) |
| | Reverse | 5' TTCTTCCATCTGCTGCCAGATGGT 3' (SEQ ID NO: 8) |
| GM-CSF | Forward | 5' GTCTCCTGAACCTGAGTAGAGACA 3' (SEQ ID NO: 11) |
| | Reverse | 5' AAGGGGATGACAAGCAGAAAGTCC3' (SEQ ID NO: 12) |
| LIF | Forward | 5' AACAACCTCATGAACCAGATCAGGAGC 3' (SEQ ID NO: 15) |
| | Reverse | 5' ATCCTTACCCGAGGTGTCAGGGCCGTAGG 3' (SEQ ID NO: 16) |
| SCF | Forward | 5' CTCCTATTTAATCCTCTCGTC 3' (SEQ ID NO: 17) |
| | Reverse | 5' TACTACCARTCTCGCTTATCCA 3' (SEQ ID NO: 18) |
| BMP-2 | Forward | 5' GGAAGAACTACCAGAAACGAG 3' (SEQ ID NO: 19) |
| | Reverse | 5' AGATGATCAGCCAGAGGAAAA 3' (SEQ ID NO: 20) |
| BMP-4 | Forward | 5' ACCTGAGACGGGGAAGAAAAA 3' (SEQ ID NO: 21) |
| | Reverse | 5' TTAAAGAGGAAACGAAAAGCA 3' (SEQ ID NO: 22) |
| IL-6 | Forward | 5' GTAGCCGCCCCACACAGACAGCC 3' (SEQ ID NO: 3) |
| | Reverse | 5' GCCATCTTTGGAAGGTTCAGG 3' (SEQ ID NO: 4) |

FIGURE 1B

| | | |
|---|---|---|
| IL-7 | Forward | 5' ATGTTCCATGTTTCTTTTAGGTATATCT 3' (SEQ ID NO: 23) |
| | Reverse | 5' TGCATTTCTCAAATGCCCTAATCCG 3' (SEQ ID NO: 24) |
| IL-8 | Forward | 5' TCTGCAGCTCTGTGTGAAGGT 3' (SEQ ID NO: 5) |
| | Reverse | 5' TGAATTCTCAGCCCTCTTCAA 3' (SEQ ID NO: 6) |
| IL-11 | Forward | 5' ATGAACTGTGTTTGCCGCCTG 3' (SEQ ID NO: 25) |
| | Reverse | 5' GAGCTGTAGAGCTCCCAGTGC 3' (SEQ ID NO: 26) |
| Flt-3 Ligand | Forward | 5' TGGAGCCCAACAACCTATCTC 3' (SEQ ID NO: 13) |
| | Reverse | 5' GGGCTGAAAGGCACATTTGGT 3' (SEQ ID NO: 14) |

FIGURE 1C

Table 3. Quantitative ELISA (pg/ml. LPS Induction of Adipose-Derived Stromal Cell Secreted Cytokines

| Time LPS | 0 Hr | 1 Hr | 2 Hr | 4 Hr | 8 Hr | 24 Hr |
|---|---|---|---|---|---|---|
| GM-CSF* | 1 ± 1 | 1 ± 0 | 3 ± 1 | 7 ± 2 | 17 ± 3 | 76* ± 28 |
| M-CSF* | 4 ± 3 | 76 ± 14 | 161 ± 29 | 304 ± 62 | 512 ± 98 | 977* ± 285 |
| IL-6* | 1 ± 1 | 287 ± 73 | 674 ± 51 | 2649 ± 495 | 6083 ± 956 | 9204 ± 2676 |
| IL-7* | 0.4 ± 0.2 | 0.4 ± 0.2 | 0.3 ± 0.3 | 0.3 ± 0.3 | 0.9 ± 0.2 | 3.4* ± 0.7 |
| IL-8* | 0 ± 0 | 88 ± 42 | 225 ± 82 | 1343 ± 224 | 4924 ± 1046 | 9710* ± 2438 |
| IL-11 | 2 ± 2 | 2 ± 1 | 13 ± 6 | 14 ± 6 | 16 ± 6 | 19 ± 8 |
| IL-12 | N.D. | N.D. | N.D. | N.D. | N.D. | N.D. |

*(Values in Table 3 are the mean ± S.E.M. from n =5 to 7 stromal cells donors. ELISAs were performed with undiluted, 1:25 or 1:125 diluted conditioned medium after the indicated exposure time to 100 ng lipopolysaccharide per ml of medium. The IL-7 ELISA is linear between 0.16 to 10 pg/ml Astericks indicate *p <0.01 between 24 hour and 0 hour time points based on one-way ANOVA. Abbreviation: N.D., not detectable.)*

FIGURE 1D

LPS Induction:

Hr:  0   4   0   4   0   4   0   4   0   4   0   4   0   4   0   4

Actin      IL-6      IL-8     G CSF     M CSF    GM CSF    Flt-3     LIF

Figure 1.
Polymerase chain reaction detection of LPS inducible cytokine mRNAs in human adipose-derived stromal cells.

FIGURE 1E

SEQUENCE LISTING

<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: PCR primers
      for Actin

<400> SEQUENCE: 1
agtaacagcc cacggtgttc                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Reverse PCR
      primer for Actin

<400> SEQUENCE: 2
agcctccgaa aggaaattgt                                              20

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: PCR primer
      for Interleukin-6

<400> SEQUENCE: 3
gtagccgccc cacacagaca gcc                                          23

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: reverse PCR
      primer for Interleukin 6

<400> SEQUENCE: 4
gccatctttg gaaggttcag g                                            21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: PCR primer
      for Interleukin 8

<400> SEQUENCE: 5
tctgcagctc tgtgtgaagg t                                            21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Reverse PCR
      primer for Interleukin 8

<400> SEQUENCE: 6

```
tgaattctca gccctcttca a                                             21

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: PCR primer
      for Granulocyte Colony Stimulating Factor

<400> SEQUENCE: 7
agcttcctgc tcaagtgctt agag                                          24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Reverse PCR
      primer for Granulocyte Colony  Stimulating Factor.

<400> SEQUENCE: 8
ttcttccatc tgctgccaga tggt                                          24

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: PCR primer
      for Macrophage Colony Stimulating Factor

<400> SEQUENCE: 9
ttgggagtgg acacctgcag tct                                           23

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Reverse PCR
      Primer for Granulocyte/Monocyte Colony Stimulating
      Factor

<400> SEQUENCE: 10
ccttggtgaa gcagctcttc agcc                                          24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: PCR primer
      for Granulocyte/Monocyte Colony Stimulating Factor

<400> SEQUENCE: 11
gtctcctgaa cctgagtaga gaca                                          24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Reverse PCR
      primer for Granulocyte/Monocyte Colony Stimulating
      Factor
```

```
<400> SEQUENCE: 12 aagggatga caagcagaaa gtcc                                              24

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: PCR primer
      for Flt3 ligand

<400> SEQUENCE: 13
tggagcccaa caacctatct c                                                21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Reverse PCR
      primer for Flt3 ligand

<400> SEQUENCE: 14
gggctgaaag gcacatttgg t                                                21

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: PCR primer
      for Leukemia Inhibitory Factor

<400> SEQUENCE: 15
aacaacctca tgaaccagat caggagc                                          27

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Reverse PCR
      primer for Leukimia Inhibitory Factor

<400> SEQUENCE: 16
atccttaccc gaggtgtcag ggccgtagg                                        29

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: PCR Primer
      Sequence for Stem Cell Factor

<400> SEQUENCE: 17
ctcctattta atcctctcgt c                                                21

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Reverse PCR
      Primer for Stem Cell Factor

<400> SEQUENCE: 18
```
tactaccatt ctcgcttatc ca                                          22

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: PCR primer
      for Bone Morphogenetic Protein 2

<400> SEQUENCE: 19
ggaagaacta ccagaaacga g                                           21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Reverse PCR
      primer for Bone Morphogenetic Protein 2

<400> SEQUENCE: 20
agatgatcag ccagaggaaa a                                           21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: PCR primer
      for Bone Morphogenetic Protein 4

<400> SEQUENCE: 21
acctgagacg gggaagaaaa a                                           21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence:  Reverse
      PCR primer for Bone Morphogenetic Protein 4

<400> SEQUENCE: 22
ttaaagagga aacgaaaagc a                                           21

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: PCR primer
      for Interleukin 7

<400> SEQUENCE: 23
atgttccatg tttcttttag gtatatct                                    28

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Reverse PCR
      primer for Interleukin 7

<400> SEQUENCE: 24

```
tgcatttctc aaatgcccta atccg                                              25

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: PCR primer
      for Interleukin 11

<400> SEQUENCE: 25
atgaactgtg tttgccgcct g                                                  21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Reverse PCR
      primer for Interleukin 11

<400> SEQUENCE: 26
gagctgtaga gctcccagtg c                                                  21
```

MULTIPLE MESODERMAL LINEAGE DIFFERENTIATION POTENTIALS FOR ADIPOSE TISSUE-DERIVED STROMAL CELLS AND USES THEREOF

CROSS-REFERENCE TO RELATED APPLICATION

This Application claims the benefit of U.S. Provisional Application No. 60/149,849 filed on Aug. 19, 1999.

FIELD OF INVENTION

This invention relates to methods and compositions for the differentiation of stromal cells from adipose tissue into hematopoietic supporting stromal cells and myocytes of both the skeletal and smooth muscle types.

BACKGROUND OF INVENTION

The neonatal period in human development is characterized by the presence of "stem" cells with the potential to develop along multiple differentiation pathways. The terminal differentiation of these cells is determined by cytokine and hormonal cues which co-ordinate organogenesis and tissue architecture. Murine embryonic stem cells have been isolated and studied extensively in vitro and in vivo. Using exogenous stimuli in vitro, investigators have induced ES cell differentiation along multiple lineage pathways. These include neuronal, B lineage lymphoid, and adipocytes (Dani et al. (1997) *J. Cell Sci.* 110: 1279; Remoncourt et al. (1998) *Mech. Dev.* 79:185; O'Shea K S (1999) *Anat. Rec.* 257:32). The ES cells have been manipulated in vivo by homologous recombination techniques to generate gene specific null or "knock-out" mice (Johnson R S (1989) *Science* 245:1234). Once ES cell clones lacking a specific gene are isolated, they are transplanted into a fertilized murine zygote. The progeny of this isolated ES cell can develop into any and all murine tissues in a coordinated manner.

A stem cell must meet the following criteria: (1) ability of a clonal stem cell population to self-renew; (2) ability of a clonal stem cell population to generate a new, terminally differentiated cell type in vitro; and (3) ability of a clonal stem cell population to replace an absent terminally differentiated cell population when transplanted into an animal depleted of its own natural cells.

Multipotential stem cells exist in tissues of the adult organism. The best characterized example of a "stem cell" is the hematopoietic progenitor isolated from the bone marrow and peripheral blood. Seminal studies by Trentin, Till and McCulloch (McCulloch et al. (1996) *Proc. Can. Cancer Conf.* 6:356–366; Curry et al. (1967) *J. Exp. Med.* 125:703–720) examined lethally irradiated mice. In the absence of treatment, these animals died because they failed to replenish their circulating blood cells; however, transplantation of bone marrow cells from a syngeneic donor animal would rescue the host animal. The donor cells were responsible for reconstituting all of the circulating blood cells. A wealth of elegant studies have gone on to demonstrate that donation of a finite number of undifferentiated hematopoietic stem cells is capable of regenerating each of the eight or more different blood cell lineages in a host. This work has provided the basis for bone marrow transplantation, a widely accepted therapeutic modality for the treatment of cancer and inborn errors of metabolism in man. Thus, hematopoietic stem cells remain present in the normal human bone marrow throughout life; they are not limited to the neonatal period.

The recent development of entire organisms from a single donor cell are consistent with this hypothesis. The "Dolly" experiment showed that cells isolated from an ovine mammary gland could develop into a mature sheep (Pennisi & Williams (1997) *Science* 275:415–1416). In similar murine studies, cells derived from the corpus luteum of the ovary could develop into a mature mouse (Pennisi (1998) *Science* 281:495). These studies suggest that stem cells with the ability to differentiate into any and all cell types continue to exist in the adult organism. Thus, "embryonic" stem cells may be retained throughout life.

In vitro experiments using cell lines of embryonic origin indicate that a mesodermal stem cell may exist. Work by Taylor and colleagues in the late 1970's demonstrated that murine embryonic fibroblasts such as C3H10T1/2 or 3T3 cells would differentiate along multiple mesodermal lineage pathways following exposure to 1 to 10 $\mu$M of 5'-azacytadine (Constantinides et al. (1977) *Nature* 267:364; Jones & Taylor (1980) *Cell* 20:85). Within 2 to 4 weeks, isolated clones displayed a morphology consistent with adipocyte, myocyte, chondrocyte or osteoblast differentiation. Biochemical data provided additional support for the identification of each of these lineages. This finding provided the basis for the identification of the master-regulatory transcription factor for skeletal muscle differentiation, myoD (Lassar (1986) *Cell* 47:649).

The adult bone marrow microenvironment is the potential source for these hypothetical mesodermal stem cells. Cells isolated from adult marrow are referred to by a variety of names, including stromal cells, stromal stem cells, mesenchymal stem cells (MSCs), mesenchymal fibroblasts, reticular-endothelial cells, and Westen-Bainton cells (Gimble et al. (1996) *Bone* 19:421–428). In vitro studies have determined that these cells can differentiate along multiple mesodermal or mesenchymal lineage pathways. These include, but are not limited to, adipocytes (fat cells) (Gimble et al. (1990) *Eur. J Immunol* 20:379-386; Pittenger et al. (1999) *Science* 284:143–147; Nuttall et al. (1998) *JBMR* 13:371–382; Park et al. (1999) *Bone* 24:549–554), chondrocytes (cartilage forming cells) (Dennis et al. (1999) *JBMR* 14:700–709), hematopoietic supporting cells (Gimble et al. (1990) *Eur. J. Immunol.* 20:379–386), myocytes (skeletal muscle) (Phinney (1999) *J. Cell. Biochem.* 72:570–585), myocytes (smooth muscle) (Remy-Martin et al. (1999) *Exp. Hematol.* 27:1782–1795), and osteoblasts (bone forming cells) (Beresford (1989) *Clin Orthop Res* 240:270–280; Owen (1988) *J. Cell. Sci.* 10:63–76; Dorheim et al. (1993) *J. Cell. Physiol.* 154:317-328; Haynesworth et al. (1992) *Bone* 13:81–88, Kuznetsov et al. (1997) *JBMR* 12:1335–1347). The bone marrow has been proposed as a source of stromal stem cells for the regeneration of bone, cartilage, muscle, adipose tissue, and other mesenchymal derived organs. The major limitations to the use of these cells are the difficulty and risk attendant upon bone marrow biopsy procedures and the accompanying loss of memory B cells and hematopoietic stem cells with present harvesting procedures.

Another viable alternative to the use of bone marrow multipotential stem cells is adipose tissue. Adipose stromal cells provide an easily accessible and abundant source of stromal cells which can differentiate along multiple mesenchymal lineages. Methods and compositions are needed for the consistent and quantitative differentiation of adipose derived stromal cells into various cell types including for example hematopoietic stromal cells and skeletal and smooth muscle myocytes.

SUMMARY OF INVENTION

Compositions and methods for the differentiation of adipocytes are provided. Generally, the present invention provides methods and compositions for consistent and quantitative induction of stromal cells derived from subcutaneous, mammary, gonadal, or omental adipose tissues into the following fully differentiated and functional mesodermal cell lineages: hematopoietic supporting stromal cells, skeletal myocytes, and smooth muscle myocytes (myofibroblasts).

The compositions include a variety of chemical components which act as mitogens and differentiation inducing agents for the plated stromal cells and yield production of the desired cell type. The mitogens and inducing agents include, but are not limited to, interleukins, flt-3 ligand, stem cell factor, macrophage-colony stimulating factor, granulocyte-monocyte colony stimulating factor, erythropoietin, thrombopoietin, osteoprotegerin ligand, dexamethasone, hydrocortisone, 1,25 dihydroxy vitamin $D_3$, 2-mercaptoethanol, glutamine, 5'-azacytadine, amphotericin, transforming growth factor β and fibroblast growth factor.

The invention provides methods for determining the ability of these compositions to direct the differentiation and function of the adipose-derived stromal cells, for the transduction of viral vectors carrying regulatory genes into stromal cells, for the transfection of plasmid vectors carrying regulatory genes into stromal cells, for the tracking and detection of functional proteins encoded by these genes, and for developing biomechanical carriers for the re-introduction of these cells into living organisms.

The invention also provides methods and compositions which have utility in drug discovery for compounds and proteins with relevance to a wide spectrum of disease states including, but not limited to, aplastic anemia, muscular dystrophy, radiation poisoning, neuropathic muscular degeneration, urogenital malformations, and gastrointestinal malformations.

BRIEF DESCRIPTION OF THE DRAWINGS

FIG. 1. Human adipose-derived stromal cells were cultured in 6 well plates until confluent and quiescent in DMEM/F 10 (1:1 vol:vol), 10% fetal bovine serum, penicillin 100 units/ml, streptomycin 100 μg/ml, and 7.5 mM HEPES pH 7.2. The cells were then incubated in DMEM/F 10 (1:1 vol:vol), 2% fetal bovine serum, penicillin 100 units/ml, streptomycin 100 μg/ml, and 7.5 mM HEPES pH 7.2 containing 100 ng/ml lipopolysaccharide (LPS). Cells were harvested immediately (time "0") or after 4 hours (time "4") for total RNA extraction and isolation using a phenol/chloroform/acid procedure (Chomczynski & Sacchi (1987) *Analytical Biochem* 162:156–159). Equal aliquots of total RNA were reverse transcribed and amplified by polymerase chain reaction with the following primer sets specific for the indicated human mRNAs; the actin primers served as a positive control for equal loading between samples:

Actin
   Forward 5' TTGGGAGTGGACACCTGCAGTCT 3' (SEQ ID NO: 1)
   Reverse 5' CCTTGGTGAAGCAGCTCTTCAGCC 3' (SEQ ID NO: 2)
M-CSF
   Forward 5' TTGGGAGTGGACACCTGCAGTCT 3' (SEQ ID NO: 9)
   Reverse 5' CCTTGGTGAAGCAGCTCTTCAGCC 3' (SEQ ID NO: 10)
G-CSF
   Forward 5' AGCTTCCTGCTCAAGTGCTTAGAGA 3' (SEQ ID NO: 7)
   Reverse 5' TTCTTCCATCTGCTGCCAGATGGT 3' (SEQ ID NO: 8)
GM-CSF
   Forward 5' GTCTCCTGAACCTGAGTAGAGACA 3' (SEQ ID NO: 11)
   Reverse 5' AAGGGGATGACAAGCAGAAAGTCC 3' (SEQ ID NO: 12)
LIF
   Forward 5' AACAACCTCATGAACCAGATCAGGAGC 3' (SEQ ID NO: 15)
   Reverse 5' ATCCTTACCCGAGGTGTCAGGGCCGTAGG 3' (SEQ ID NO: 16)
SCF
   Forward 5' CTCCTATTTAATCCTCTCGTC 3' (SEQ ID NO: 17)
   Reverse 5' TACTACCARTCTCGCTTATCCA 3' (SEQ ID NO: 18)
BMP-2
   Forward 5' GGAAGAACTACCAGAAACGAG 3' (SEQ ID NO: 19)
   Reverse 5' AGATGATCAGCCAGAGGAAAA 3' (SEQ ID NO: 20)
BMP-4
   Forward 5' ACCTGAGACGGGGAAGAAAAA 3' (SEQ ID NO: 21)
   Reverse 5' TTAAAGAGGAAACGAAAAGCA 3' (SEQ ID NO: 22)
IL-6
   Forward 5' GTAGCCGCCCCACACAGACAGCC 3' (SEQ ID NO: 3)
   Reverse 5' GCCATCTTTGGAAGGTTCAGG 3' (SEQ ID NO: 4)
IL-7
   Forward 5' ATGTTCCATGTTTCTTTTAGGTATATCT 3' (SEQ ID NO: 23)
   Reverse 5' TGCATTTCTCAAATGCCCTAATCCG 3' (SEQ ID NO: 24)
IL-8
   Forward 5' TCTGCAGCTCTGTGTGAAGGT 3' (SEQ ID NO: 5)
   Reverse 5' TGAATTCTCAGCCCTCTTCAA 3' (SEQ ID NO: 6)
IL-11
   Forward 5' ATGAACTGTGTTTGCCGCCTG 3' (SEQ ID NO: 25)
   Reverse 5' GAGCTGTAGAGCTCCCAGTGC 3' (SEQ ID NO: 26)
Flt-3-
   Forward 5' TGGAGCCCAACAACCTATCTC 3' (SEQ ID NO: 13)
Ligand
   Reverse 5' GGGCTGAAAGGCACATTTGGT 3' (SEQ ID NO: 14)

The resulting PCR products were electrophoresed on a 2% agarose gel, stained with ethidium bromide and photographed.

Table 1. Characterization of Adipose Derived Stromal Cell Surface Markers Based on Antibody and PCR Detection. The listed cell surface proteins and genes analyzed in human adipose derived stromal cells is based on immunohistochemical staining, flow cytometry, and/or by polymerase chain reaction. Markers are divided among those expressed (listed as "positive") and not expressed (listed as "negative").

Table 2. Cytokines Expressed by Adipose-Derived Stromal Cells Constitutively or Following Endotoxin (LPS) Induction. The listed cytokines were analyzed in total RNA isolated from human adipose derived stromal cells following induction with 100 ng/ml of lipopolysaccharide. The cytokines listed in the table were detected using the oligonucleotide primers listed. All cytokines were expressed either in a constitutive or inducible manner.

Table 3. Quantitative ELISA (pg/ml) LPS Induction of Adipose-Derived Stromal Cell Secreted Cytokines. The listed cytokines were assayed in conditioned medium from human adipose derived stromal cells induced for 0 to 24 hours with 100 ng/ml of LPS. All cytokines were detected by enzyme linked immunoassay (ELISA) and are expressed as pg/ml of conditioned medium. Those cytokines indicated by an "*" demonstrated significant increases relative to the 0 hour time point within the 24 hour induction period based on one way analysis of variance.

DETAILED DESCRIPTION OF THE INVENTION

The present invention provides methods and compositions for the differentiation and culture of adipose tissue-derived stromal cells into (a) hematopoietic supporting stromal cells, (b) skeletal myocytes, and (c) smooth muscle myocytes (myofibroblasts).

Adipose tissue offers a potential alternative to the bone marrow as a source of multipotential stromal stem cells. Adipose tissue is readily accessible and abundant in many individuals. Obesity is a condition of epidemic proportions in the United States, where over 50% of adults exceed the recommended BMI based on their height. Adipocytes can be harvested by liposuction on an outpatient basis. This is a relatively non-invasive procedure with cosmetic effects which are acceptable to the vast majority of patients. It is well documented that adipocytes are a replenishable cell population. Even after surgical removal by liposuction or other procedures, it is common to see a recurrence of adipocytes in an individual over time. This suggests that adipose tissue contains stromal stem cells which are capable of self-renewal. Pathologic evidence suggests that adipose-derived stromal cells are capable of differentiation along multiple mesenchymal lineages. The most common soft tissue tumor, liposarcomas, develop from adipocyte-like cells. Soft tissue tumors of mixed origin are relatively common. These may include elements of adipose tissue, muscle (smooth or skeletal), cartilage, and/or bone. Just as bone forming cells within the bone marrow can differentiate into adipocytes or fat cells, the extramedullary adipocytes are capable of forming bone. In patients with a rare condition known as paroxysmal osseous heteroplasia, subcutaneous adipocytes form bone for unknown reasons (Kaplan (1996) *Arch. Dermatol.* 132:815–818).

Adult human extramedullary adipose tissue-derived stromal cells represent a stromal stem cell source which can be harvested routinely with minimal risk to the patient. They can be expanded ex vivo, differentiated along unique mesodermal lineage pathways, genetically engineered, and re-introduced into individuals as either an autologous or allogeneic transplantation. This invention presents examples of methods and composition for the isolation, characterization, and differentiation of adult human extramedullary adipose tissue stromal cells along the mesodermal lineages and outlines their use for the treatment of a number of human conditions and diseases.

The cells produced by the methods of invention are useful in providing a source of fully differentiated and functional cells for research, transplantation, and development of tissue engineering products for the treatment of human disease and traumatic injury repair. Thus, in one aspect, the invention provides a method for differentiating adipose lineages: hematopoietic supporting cells, myocytes (skeletal), and myocytes (smooth muscle myofibroblasts) comprising: culturing said cells in a composition which comprises a medium (a) capable of supporting the growth of stromal cells and hematopoietic cells in co-culture with factors present capable of inducing stromal expression of hematopoietic growth factors or the addition of exogenous growth factors directly; (b) capable of supporting the growth and differentiation of stromal cells into functional and proliferating skeletal myocytes; and (c) capable of supporting the growth and differentiation of stromal cells into functional and proliferating smooth muscle myocytes or myofibroblasts.

In another aspect, the invention provides compositions for the differentiation of adipose tissue-derived stromal cells into each of the three different mesodermal derived lineages. Such compositions comprise:

(a) adipose tissue-derived stromal cells, a medium capable of supporting the growth of the stromal cells, and growth factors and agents capable of inducing stromal cell expression of hematopoietic growth factors or exogenous hematopoietic growth factors or non-peptide factors themselves.

(b) adipose tissue-derived stromal cells, a medium capable of supporting the growth of the stromal cells, and amounts of 5' azacytadine and/or amphotericin or other agents sufficient to induce the differentiation of said stromal cells into skeletal muscle myocytes.

(c) adipose tissue-derived stromal cells, a medium capable of supporting the growth of the stromal cells, and amounts of transforming growth factor $\beta$ or other peptide growth factors sufficient to induce the differentiation of said stromal cells into smooth muscle myocytes or myofibroblasts.

The methods comprise incubation of isolated adipose tissue-derived stromal cells, plated at densities of about 1,000 to 25,000 cells/cm$^2$ in medium consisting of the following for each lineage:

(a) Hematopoietic supporting stromal cell—Glucose, hematopoietic inducing cytokines, including but not limited to, interleukins-1, 3, 6, 7, 11, 12, stem cell factor, flt-3 ligand, macrophage colony stimulating factor, granulocyte-monocyte colony stimulating factor, thrombopoietin, erythropoietin, osteoprotegerin ligand, 1,25 dihydroxy vitamin D$_3$, and 2-mercaptoethanol. The medium may also contain hydrocortisone, dexamethasone, and osteoprotegerin ligand. Cells are maintained at temperatures of 33° C. (for myeloid cells) or 37° C. (for B-lineage lymphoid cells).

(b) Myocytes, Skeletal—Glucose, 5'-azacytadine or amphotericin for a limited exposure period with manipulation of fetal bovine serum of concentrations between 0% and 20%. The medium may also include, but is not limited to, an antibiotic(as for example penicillin or streptomycin), glutamine, sodium pyruvate, and 2-mercaptoethanol.

(c) Myocytes, Smooth Muscle/Myofibroblasts—Glucose and 10% fetal bovine serum in the presence of a collagen, gelatin, laminin, fibronectin or other susbtratum or 3-dimensional matrix.

"Adipose stromal cells" refers to stromal cells that originate from adipose tissue. By "adipose" is meant any fat tissue. The adipose tissue may be brown or white adipose tissue, derived from subcutaneous, omental/visceral, mammary, gonadal, or other adipose tissue site. Preferably, the adipose is subcutaneous white adipose tissue. Such cells may comprise a primary cell culture or an immortalized cell line. The adipose tissue may be from any organism having fat tissue. Preferably, the adipose tissue is mammalian, most preferably the adipose tissue is human. A convenient source of adipose tissue is from liposuction surgery, however, the source of adipose tissue or the method of isolation of adipose tissue is not critical to the invention. If stromal cells are desired for autologous transplantation into a subject, the adipose tissue will be isolated from that subject.

"Hematopoietic supporting stromal cell" refers to stromal cells that are capable of supporting the proliferation and maturation of hematopoietic progenitor, also known as hematopoietic stem cells, derived from bone marrow, spleen, peripheral blood, or umbilical blood, either CD34+ or CD34−. Co-cultures of hematopoietic supporting stromal cells with hematopoietic progenitors would result in the production of both adherent and non-adherent populations of hematopoietic blood cells, including but not limited to myeloid (macrophage, neutrophil, osteoclast), erythroid (red blood cells), lymphoid (B-lymphoid, T-lymphoid), and platelet (megakaryocyte), as well as eosinophils, basophils, mast cells and other circulating blood cell types. Growth and differentiation of hematopoietic cells will be determined by assays which include, but are not limited to, those that assess the surface expression of characteristic blood cell lineage specific proteins (such as CD45 for B lineage lymphocytes, T cell receptor for T lineage lymphocytes, Mac-I/LFA11 for macrophages, tartrate resistant acid phosphatase for osteoclasts). Proliferation of hematopoietic stem cells will be assessed in vitro by evidence that co-culture derived hematopoietic cells can continue to expand to multiple blood cell lineages when plated onto a fresh hematopoietic supporting stromal cell layer and in vivo based on the ability of co-culture derived hematopoietic cells to repopulate the bone marrow and rescue a lethally irradiated animal host lacking its own blood cells.

"Myocytes (skeletal)" refers to cells that are capable of expressing characteristic biochemical markers of skeletal muscle, including but not limited to the transcription factors myoD and myogenin, skeletal actin, myosin light chain kinase, and myosin heavy chain kinase, characteristic morphologic markers of skeletal muscle, including but not limited to multinucleated complexes and sarcomeres, and able to exhibit contractile function spontaneously or in response to exogenous factors such as acetylcholine. "Myocytes (smooth muscle, myofibroblasts)" refers to cells that are capable of expressing characteristic biochemical markers of smooth muscle, including but not limited to α-smooth muscle actin, fibronectin, and β-1 integrin, characteristic morphologic markers of smooth muscle, including but not limited to the formation of stress fibers in culture, and able to exhibit characteristic smooth muscle functions, including but not limited to the generation of tensile stress on collagen lattices in vitro.

"Hematopoietic growth factors" refers to cytokines, hormones and other protein agents. These may be derived directly from stromal cells in the co-culture system or added to co-cultures at concentrations determined by the investigator and obtained as enriched or purified proteins developed from recombinant or natural sources. These will include but are not limited to the following cytokines and hormones: interleukin 7 for the growth of B lineage lymphocytes; stem cell factor for all hematopoietic lineages; M-CSF for macrophages and osteoclasts; osteoprotegerin ligand for osteoclasts; erythropoeitin for erythrocytes; thrombopoietin for platelets and megakaryocytes; interleukin 6 for platelets, megakaryocytes, and B lineage lymphocytes. Optimal concentrations and length of treatment may be determined by the practitioner through the use of known assays for the differentiation of each blood cell lineage.

"Non-peptide growth factors" refers to steroids, retinoids and other chemical compounds or agents which induce the differentiation of blood cell lineages. It is generally recognized that concentrations may vary. Moroever, it is generally recognized that the compounds or agents will be added in amounts sufficient to stimulate differentiation. Generally, however, these will be used at concentrations ranging from about 1 nM to about 100 nM for 1,25 dihydroxy vitamin $D_3$, about 1 nM to about 100 nM dexamethasone, about 1 nM to about 100 nM hydrocortisone, about 1 nM to about 100 nM retinoic acid, about 1 nM to about 100 nM 9-cis retinoic acid, or at concentrations to be determined and optimized by the practitioner.

Amounts of 5' azacytadine and/or amphotericin sufficient to induce differentiation refers to concentrations of 5' azacytadine and amphotericin, that when supplied in a medium capable of supporting the growth of stromal cells (e.g. NIH-3T3, C3H 10T1/2, human adipose tissue-derived stromal cells and the like), will induce the differentiation of said stromal cells into skeletal muscle myoblasts and myocytes over a period of about 1 to 6 weeks. Typical use concentrations for 5'azacytadine range from about 1 $\mu$M to about 30 $\mu$M. Typical use concentrations for amphotericin range from about 10 ng/ml to about 100 ng/ml. Optimal concentrations and length of exposure may be determined by the practitioner through the use of known assays for the differentiation of skeletal muscle myoblasts. Such assays include, but are not limited to, those that assess the morphological or biochemical characteristics associated with skeletal muscle (e.g., formation of multinucleated myotubules, expression of myosin heavy chain, expression of myoD at the protein or RNA level).

"Amounts of transforming growth factor β or other peptide growth factors sufficient to induce differentiation" refers to concentrations of transforming growth factor β or other peptides, that when supplied to medium capable of supporting the growth of stromal cells (e.g. NIH-3T3, C3H 10T1/2, human adipose tissue-derived stromal cells and the like), will induce the differentiation of said stromal cells into smooth muscle myocytes or myofibroblasts over a period of 1 day to 6 weeks. Typical use concentrations for transforming growth factor β range from about 20 ng/ml to about 40 ng/ml. Typical use concentrations for fibroblast growth factor range from about 20 ng/ml to about 40 ng/ml. Optimal concentrations and length of exposure may be determined by the practitioner through the use of known assays for the differentiation of smooth muscle myoblasts. Such assays include, but are not limited to, those that assess the morphological or biochemical characteristics associated with smooth muscle (e.g., expression of α smooth muscle actin and fibronectin, generation of contractile forces when placed in collagen lattices in the presence of thrombin or lysophosphatidic acid).

Any medium capable of supporting stromal cells in tissue culture may be used. Media formulations that will support the growth of fibroblasts include, but are not limited to, Dulbecco's Modified Eagle's Medium (DMEM), alpha modified Minimal Essential Medium (αMEM), and Roswell Park Memorial Institute Media 1640 (RPMI Media 1640) and the like. Typically, 0 to 20% Fetal Bovine Serum (FBS)

will be added to the above media in order to support the growth of stromal cells and hematopoietic cells. However, a defined medium could be used if the necessary growth factors, cytokines, and hormones in FCS for stromal cell and hematopoietic cell growth are identified and provided at appropriate concentrations in the growth medium.

Media useful in the methods of invention may contain one or more compounds of interest, including, but not limited to, antibiotics, compounds that are mitogenic for hematopoietic; stem cells, differentiation inducing for hematopoietic stem cells, and/or mitogenic or differentiative for stromal cells. Example of antibiotics useful in the invention include but are not limited to penicillin and streptomycin. Penicillin is typically used at about 10 units/ml to about 200 units/ml. Streptomycin is typically used at about 10 µg/ml to 200 µg/ml. Examples of hematopoietic mitogenic factors include but are not limited to stem cell factor and interleukin 3; hematopoietic differentiation inducing factors include but are not limited to 1,25 dihydroxy vitamin $D_3$, interleukin 7, and osteoprotegerin ligand; stromal cell mitogens include but are not limited to transforming growth factor β; and stromal cell differentiating factors include but are not limited to dexamethasone, hydrocortisone, transforming growth factor β, and the like.

"Adipose tissue-derived stromal cells, a medium capable of supporting the growth of the stromal cells, and growth factors and agents capable of inducing stromal cell expression of hematopoietic growth factors or exogenous hematopoietic growth factors or non-peptide factors themselves" refers to growth factors, both peptide and chemical in composition, which enhance the proliferation and maturation of hematopoietic stem cells in vitro and in vivo. These include, but are not limited to, interleukin 1, interleukin 3, interleukin 6, interleukin 7, interleukin 11, macrophage colony stimulating factor (M-CSF), granulocyte-monocyte colony stimulating factor (GM-CSF), stem cell factor, flt3 ligand, thrombopoietin, erythropoietin, osteoprotegerin ligand, dexamethasone, hydrocortisone, and 1,25 dihydroxy vitamin $D_3$. The concentrations of these factors and the length of time of exposure will be determined and optimized by the investigators. Interleukins, M-CSF, GM-CSF, Flt 3 ligand and stem cell factor are used at about 5 pg/ml to about 1 ng/ml. Thrombopoietin is typically used at concentrations ranging from about 5 pg/ml to about 1 ng/ml. Erythropoietin is used at about 5 units/ml to about 1000 units/ml. Osteoprotegerin ligand is used at about 5 pg/ml to about 1 ng/ml. Dexamethasone, hydrocortisone, and 1,25 dihydroxy vitamin $D_3$ are at concentrations from about 1 nM to about 100 nM. Optimal concentrations and treatment times will be determined by monitoring the production of specific circulating blood cell lineages in the co-cultures of hematopoietic stem cells and adipose tissue-derived stromal cells. It is generally recognized that these factors will be added in amounts sufficient to stimulate differentiation. Such assays and indices include, but are not limited to, those that assess the morphological or biochemical characteristics of the cells, such as the expression of cell surface proteins unique to specific blood cell lineages by flow cytometry, immunohistochemistry, and/or immunofluorescent methods, expression of specific mRNAs in the cell population, or by in vivo assessment of the production of hematopoietic stem cells by the co-culture system.

"Adipose tissue-derived stromal cells, a medium capable of supporting the growth of the stromal cells, and amounts of azacytadine and/or amphotericin or other agents sufficient to induce the differentiation of said stromal cells into skeletal muscle myocytes" refers to the differentiation inducing agents used to promote expression of skeletal muscle specific gene markers and skeletal muscle function in vitro. The medium comprises fetal bovine serum, antibiotic, L-glutamine, sodium pyruvate, 2-mercaptoethanol, and 5' azacytadine or amphotericin. Fetal bovine serum can be used at concentrations ranging from 0.5% to 20%. The antibiotic typically used, but not limited to, is penicillin or streptomycin. Penicillin is typically used at concentrations ranging from about 10 units/ml to about 200 units/ml. Streptomycin is typically used in concentrations ranging from about 10 µg/ml to about 200 µg/ml. L-glutamine and sodium pyruvate are typically used at 0.5 mM to about 2 mM. 2-mercaptoethanol is typically used at about 10 µM to about 100 µM. 5' azacytadine is typically used at about 1 µM to about 30 µM. Amphotericin is typically used at about 10 ng/ml to about 100 ng/ml. The concentrations of these factors and the length of time of exposure will be determined and optimized by the investigators. Optimal concentration and treatment times will be determined by monitoring the morphologic and biochemical markers characteristic of skeletal muscle. These include, but are not limited to, the production of multi-nucleated myotubules in culture and the expression of muscle specific genes and proteins, such as muscle transcription factors (myoD, myogenin), myosin light chain kinase, myosin heavy chain kinase, and skeletal muscle actin.

"Adipose tissue-derived stromal cells, a medium capable of supporting the growth of the stromal cells, and amounts of transforming growth factor β or other peptide growth factors sufficient to induce the differentiation of said stromal cells into smooth muscle myocytes or myofibroblasts" refers to the differentiation inducing conditions used to promote the expression of smooth muscle associated gene markers and proteins and smooth muscle function in vitro. The concentrations of factors and the length of time of exposure will be determined and optimized by the investigators. Optimal concentration and treatment times will be determined by monitoring the morphologic and biochemical markers characteristic of smooth muscle cells. These include, but are not limited to, the generation of tensile forces by the cells when placed in a collagen type I lattice and the expression of smooth muscle specific genes and proteins, such as smooth muscle actin, fibronectin, and laminin.

Preferably, the adipose tissue derived stromal cells are isolated from the adipose tissue of the subject into which the final differentiated cells are to be introduced. However, the stromal cells may also be isolated from any organism of the same or different species as the subject. Any organism with adipose tissue can be a potential candidate. Preferably, the organism is mammalian, most preferably the organism is human.

The adipose tissue derived stromal cells may be stably or transiently transfected or transduced with a nucleic acid of interest using a plasmid, viral or alternative vector strategy. Nucleic acids of interest include, but are not limited to, those encoding gene products which; (1) enhance the growth, differentiation, maturation and proliferation of hematopoietic cell lineages; examples include osteoprotegerin ligand which induces osteoclast development, interleukin 7, which induces B lineage lymphocyte development, erythropoietin, which induces erythrocyte development, and thrombopoietin, which induces platelet development; (2) enhance the differentiation of skeletal muscle; examples include myoD and myogenin, transcription factors which promote myotubule formation and expression of skeletal muscle specific genes; (3) enhance the growth, differentiation and maturation of smooth muscle cells; examples include transforming growth factor β, which induces smooth muscle proliferation and extracellular matrix production.

The blood cells produced by in vitro co-cultures of hematopoietic stem cells and adipose tissue derived stromal cells can be introduced alone or in combination with the stromal component into subjects subject to anemia or limited blood cell production. These may include, but are not limited to, patients receiving high dose chemotherapy, patients undergoing bone marrow transplantation, patients suffering from aplastic anemia, patients suffering from sickle cell anemia, and other blood dyscrasias.

Other disorders which may be treated with infusion of stem cells include, but are not limited to, diseases resulting from a failure or a dysfunction of normal blood cell production and maturation (i.e., aplastic anemia and hypoproliferative stem cell disorders); neoplastic, malignant diseases in the hematopoietic organs (e.g., leukemia and lymphomas); broad spectrum malignant solid tumors of non-hematopoietic origin; autoimmune conditions; and genetic disorders. Such disorders include, but are not limited to diseases resulting from a failure or dysfunction of normal blood cell production and maturation hyperproliferative stem cell disorders, including a plastic anemia, pancytopenia, agranulocytosis, thrombocytopenia, red cell aplasia, Blackfan-Diamond syndrome, due to drugs, radiation, or infection, idiopathic; hematopoietic malignancies including acute lymphoblastic (lymphocytic) leukemia, chronic lymphocytic leukemia, acute myelogenous leukemia, chronic myelogenous leukemia, acute malignant myelosclerosis, multiple myeloma, polycythemia vera, agnogenic myelometaplasia, Waldenstrom's macroglobulinemia, Hodgkin's lymphoma, non-Hodgkin's lymphoma; immunosuppression in patients with malignant, solid tumors including malignant melanoma, carcinoma of the stomach, ovarian carcinoma, breast carcinoma, small cell lung carcinoma, retinoblastoma, testicular carcinoma, glioblastoma, rhabdomyosarcoma, neuroblastoma, Ewing's sarcoma, lymphoma; autoimmune diseases including rheumatoid arthritis, diabetes type 1, chronic hepatitis, multiple sclerosis, systemic lupus erythematosus; genetic (congenital) disorders including anemias, familial aplastic, Fanconi's syndrome, Bloom's syndrome, pure red cell aplasia (PRCA), dyskeratosis congenita, Blackfan-Diamond syndrome, congenital dyserythropoietic syndrome I–IV, Chwachmann-Diamond syndrome, dihydrofolate reductase deficiencies, formanino transferase deficiency, Lesch-Nyhan syndrome, congenital spherocytosis, congenital elliptocytosis, congenital stomatocytosis, congenital Rh null disease, paroxysmal nocturnal hemoglobinuria, G6PD (glucose-6-phosphate dehydrogenase) variants 1, 2, 3, pyruvate kinase deficiency, congenital erythropoietin sensitivity, deficiency, sickle cell disease and trait, thalassemia alpha, beta, gamma, met-hemoglobinemia, congenital disorders of immunity, severe combined immunodeficiency disease (SCID), bare lymphocyte syndrome, ionophore-responsive combined immunodeficiency, combined immunodeficiency with a capping abnormality, nucleoside phosphorylase deficiency, granulocyte actin deficiency, infantile agranulocytosis, Gaucher's disease, adenosine deaminase deficiency, Kostmann's syndrome, reticular dysgenesis, congenital leukocyte dysfunction syndromes; and others such as osteopetrosis, myelosclerosis, acquired hemolytic anemias, acquired immunodeficiencies, infectious disorders causing primary or secondary immunodeficiencies, bacterial infections (e.g., Brucellosis, Listerosis, tuberculosis, leprosy), parasitic infections (e.g., malaria, Leishmaniasis), fungal infections, disorders involving disproportions in lymphoid cell sets and impaired immune functions due to aging, phagocyte disorders, Kostmann's agranulocytosis, chronic granulomatous disease, Chediak-Higachi syndrome, neutrophil actin deficiency, neutrophil membrane GP-180 deficiency, metabolic storage diseases, mucopolysaccharidoses, mucolipidoses, miscellaneous disorders involving immune mechanisms, Wiskott-Aldrich Syndrome, alpha 1-antitrypsin deficiency, etc.

The skeletal muscle cells produced by in vitro manipulation of the adipose tissue derived stromal cells can be introduced alone or in combination with a composition matrix to repair muscle defects secondary to metabolic diseases (muscular dystrophy, myositis), trauma, and disuse atrophy. Such compositions include, but are not limited to, collagen matrices, poly-lactic polymers, poly-glycolic polymers, alginate, or other solid supports.

The smooth muscle cells produced by in vitro manipulation of the adipose tissue derived stromal cells can be introduced alone or in combination with a composition matrix to repair smooth muscle defects. These defects may include, but are not limited to, urinary bladder wall abnormalities due to hereditary malformations in neonates or secondary to trauma or tumor invasion in older individuals, gastrointestinal tract abnormalities due to hereditary malformations in neonates or secondary to trauma or tumor invasion in older individuals, genital tract abnormalities (vaginal) due to hereditary malformations in neonates, secondary to trauma or tumor invasion, or for tissue reconstructive surgeries in transgender operations, or for the development of functional large veins for grafting purposes. Composition matrices may include, but are not limited to, collagen matrices such as swine intestinal submucosa, poly-lactic polymers, poly-glycolic polymers, alginate, or other solid supports.

Another object of the invention is to provide methods for the identification and study of compounds that enhance or inhibit the differentiation of adipose tissue derived stromal cells into either hematopoietic supporting stromal cells, skeletal muscle myocytes, or smooth muscle myocytes. Compounds which enhance differentiation. (a) hematopoietic supporting stromal cell function may be of value in the treatment of blood dyscrasias characterized by decreased production of circulating blood cells and improve recovery of patients following high dose chemotherapy; (b) skeletal muscle myocytes may be of value in the treatment of musculoskeletal diseases secondary to hereditary defects or trauma; or (c) smooth muscle myocytes may be of value in the treatment of smooth muscle defects, including those of the urinary bladder (bladder wall), gastrointestinal tract (colon, small intestine), and genital system (vaginal). Conversely, compounds which inhibit differentiation of (a) hematopoietic supporting stromal cells may be of value in the treatment of blood dyscrasias characterized by overproduction of circulating blood cells, such as polycythemia vera; (b) skeletal muscle may be of value in the treatment of soft tissue tumors of skeletal muscle origin, such as rhabdomyosarcomas; and (c) smooth muscle may be of value in the treatment of soft tissue tumors of smooth muscle origin, such as leiomyosarcomas.

Any compound may be tested for its ability to affect the differentiation of of adipose tissue derived stromal cells into either hematopoietic supporting stromal cells, skeletal muscle myocytes, or smooth muscle myocytes. Appropriate vehicles compatible with the compound to be tested are known to those skilled in the art and may be found in the current edition of Remington's Pharmaceutical Sciences, the contents of which are incorporated herein by reference.

The features and advantages of the present invention will be more clearly understood by reference to the following examples, which are not to be construed as limiting the invention.

EXAMPLES

Example 1

Expression of Cell Surface Adhesion Molecules and Hematopoietic Cytokines by Adipose Tissue-Derived Stromal Cells in vitro Stromal cells are isolated from human subcutaneous adipose tissue according to methods described in "Methods and Compositions for the Differentiation of Human Preadipocytes into Adipocytes" Ser. No. 09/240,029, filed Jan. 29, 1999. These cells are plated at a density of 30,000 cells per $cm^2$ in chamber slides, in 6 well tissue culture plates, or in T25 $cm^2$ flasks. Cells are maintained in culture for 8 days in DMEM/Ham's F-10 supplemented with 10% fetal bovine serum, penicillin 100 units/ml, streptomycin 100 µg/ml, and 7.5 mM HEPES pH 7.2. The surface proteins expressed by the stromal cells are determined by immunologic techniques based on immunohistochemistry and/or flow cytometry. For immunohistochemical analysis, chamber slides are fixed using 95% ethanol/5% glacial acetic acid and incubated with murine monoclonal antibodies detecting human cell surface proteins. After incubation with an enzyme coupled anti-mouse secondary antibody, evidence of protein expression is detected by histochemical reaction. Alternatively, flasks of cells are harvested by trypsin/EDTA digestion and incubated with a fluorescent conjugated murine monoclonal antibody detecting a specific human surface protein. Cells are examined for fluorescent intensity by flow cytometry. The results of these assays are summarized in Table 1. These studies demonstrate that adipose-derived stromal cells express cell surface proteins associated with and essential for hematopoietic support function by bone marrow stromal cells (Miyake et al. (1990) *J Exp Med* 171:477–488; Miyake et al. (1991) *J Exp Med* 173:599–607; Miyake et al. (1991) *J Cell Biol* 114:557–565, 1991; Jacobsen et al. (1992) *J Exp Med* 176:927–935; Kincade et al. (1993) *Curr Top Microbiol Immunol* 184:215–222; Hayashi et al. (2000) *Leuk Lymphoma* 38:265–270) these include VCAM1, CD44, integrin β1, integrin α4,5 (VLA-4, VLA-5), and CD9, among others.

The cytokine expression profile of the adipose-derived stromal cells is determined following induction with lipopolysaccharide (LPS) or endotoxin, an inflammatory agent capable of inducing hematopoietic cytokines in bone marrow stromal cells (Gimble et al. (1989) *Blood* 74:303–311). Confluent and quiescent cultures of cells are exposed to 100 ng/ml LPS for periods of 0 to 24 hours in DMEM medium supplemented with 2% fetal bovine serum, 100 µg/ml streptomycin, 100 units/ml penicillin, and 7.5 mM HEPES pH 7.2. The conditioned medium from each culture is harvested and stored at −80° C. while the total RNA is harvested by the method of Chomczynski and Sacchi (See *Anal. Biochem.* (1987)162:156–159). The mRNA for the cytokines indicated in Table 2 is detected by polymerase chain reaction using the oligonucleotide primer sets listed below the table. A representative set of reactions is demonstrated in FIG. 1. The following cytokines demonstrated significant LPS inducible expression of immunoreactive protein based on enzyme linked immunoassay: macrophage colony stimulating factor (M-CSF), granulocyte/monocyte colony stimulating factor (GM-CSF), interleukin 6, 7, and 8 (IL-6, 7, 8). The profile of cytokines expressed by the adipose derived stromal cells is consistent that of bone marrow-derived stromal cells capable of supporting myeloid, lymphoid, and osteoclast proliferation and differentiation in vitro (Pietrangeli et al. (1988) *Eur. J. Immunol.* 18:863–872; Gimble et al. (1989) *Blood* 74:303–311; Gimble et al. (1992) *J. Cell Biochem* 50:73–82; Kelly et al. (1998) *Endocrinol.* 139:2092–2101).

Example 2

Establishment of Myelopoietic Co-Cultures with an Adipose Tissue-Derived Stromal Cells Layer in vitro Stromal cells are isolated from human subcutaneous adipose tissue according to methods described in "Methods and Compositions for the Differentiation of Human Preadipocytes into Adipocytes" Ser. No. 09/240,029, filed Jan. 29, 1999. These cells are plated at a density of 500 to 20,000 cells per $cm^2$. Stromal cells are established in the cultures for 1 to 3 days prior to the introduction of hematopoietic progenitor cells into the co-culture system. Hematopoietic progenitor cells are isolated from one of the following human tissues: bone marrow, umbilical vein/placental blood, peripheral blood, spleen. Alternatively, murine tissues are used. Murine bone marrow cells are harvested by flushing the marrow cavity of 6 to 10 week old mice with DMEM/10% FCS under sterile conditions. Murine spleen cells are harvested by physical passage through a fine metal screen under sterile conditions. One of three methods are used to deplete the mixed hematopoietic cell population of its stromal component. As a first alternative, the hematopoietic stem cell population from the blood sample will be enriched by magnetic immunobead purification using anti-CD34 antigen according to established techniques. As a second alternative, hematopoietic cells will be enriched by passage of the bone marrow or other blood sample over a sterile G-10 Sephadex or nylon wool column; hematopoietic progenitor cells are eluted while stromal cells are retained. As a third alternative, hematopoietic cells will be enriched by flow cytometric sorting based on surface protein characteristics. The hematopoietic cells are washed once and the number of nucleated cells is counted using a hematocytometer after erythrocyte lysis with 0.3% acetic acid and trypan blue staining. Hematopoietic cells are introduced into the liquid co-cultures at a ratio of preferably 10 to 100 nucleated hematopoietic cells per stromal cell plated, more preferably 20 to 30 nucleated hematopoietic cells per stromal cell plated, most preferably 25 to 30 nucleated hematopoietic cells per stromal cell plated. Cells are cultured in a medium consisting of DMEM (high glucose), 10% fetal bovine serum supplemented with 10 to 100 nM hydrocortisone or 10% horse serum, 10 to 200 units/ml of penicillin, 10 to 200 µg of streptomycin at 33° C. in 5% $CO_2$. One half of the medium in the co-cultures is replaced every 3 to 4 days. The number of non-adherent cells in the medium is determined by hematocytometer count and/or by flow cytometery. The surface antigen characteristics of the non-adherent cells are documented using routine antibody markers for the major hematopoietic cell lineages. These will include, but are not limited to, Mac-1, Thy 1, Ig Heavy chain, Ter-81 (erythroid marker). The number and character of the non-adherent cell population is determined over a period of up to 10 weeks. At the conclusion of the study, the cellular composition of the adherent cell layer is determined by flow cytometric or immunohistochemical methods. As an alternative approach, the hematopoietic studies are conducted in semi-solid cultures. Cells are prepared as described above, but the hematopoietic progenitor cells are plated in the additional presence of 2.1% methylcellulose. Colony formation is assessed after a 7 to 14 day period for the presence of granulocytes, erythrocytes, macrophages, and monocytes using histologic, morphologic and immunologic criteria.

Example 3

Ability of Adipose Tissue Derived Stromal Cell/ Hematopoietic Progenitor Cell Co-Cultures to Maintain Proliferation of Hematopoietic Progenitors In vitro Adipose tissue derived stromal cell/hematopoietic progenitor co-cultures established under liquid culture conditions described in Example 1 are used to assess the ability of this system to maintain the proliferation of the hematopoietic progenitor cells in vitro. Co-cultures are established using human adipose tissue derived stromal cells and murine hematopoietic progenitors. Cultured cells are transduced with a viral vector expressing a traceable protein marker such as green fluorescent protein or beta-galactosidase. Alternatively, co-culture cells are identified by expression of a unique antigen or genetic marker due to their origin; e.g., the expression of human proteins for the stromal cells, and the expression of a transgenic or male gender specific marker for the murine hematopoietic cells. Established co-cultures are harvested by limited incubation with trypsin/ EDTA and infused into a lethally irradiated immunodeficient mouse. Animals will be followed over time. After 9 to 14 days, mice are sacrificed and their spleens examined for the appearance of hematopoietic cell islands or splenic colony forming units (CFU-S). Alternatively, mice will be maintained for 14 days or longer and their circulating blood cell count determined by hematologic and flow cytometric assays. The presence of specific markers of the stromal cells and the donor hematopoietic cells is detected with antibody reagents or specific DNA markers on fixed cells, either by flow cytometry or conventional pathologic/histologic methods. The ability of the co-cultured cells to establish CFU-S in the recipient and/or to maintain the proliferation and maturation of donor blood cells in the host after 14 days is evidence of the continued expansion of some hematopoietic progenitors in vitro by the adipose tissue-derived stromal cells.

Example 4

Establishment of Lymphopoietic Co-Cultures with an Adipose Tissue-Derived Stromal Cells Layer in vitro Stromal cells are isolated from human subcutaneous adipose tissue according to methods described in "Methods and Compositions for the Differentiation of Human Preadipocytes into Adipocytes" Ser. No. 09/240,029, filed Jan. 29, 1999. These cells are plated at a density of 500 to 20,000 cells per cm². Stromal cells are established in the cultures for 1 to 3 days prior to the introduction of hematopoietic progenitor cells into the co-culture system. Hematopoietic progenitor cells are isolated from one of the following human tissues: bone marrow, umbilical vein/placental blood, peripheral blood, spleen. Alternatively, murine tissues are used. Murine bone marrow cells are harvested by flushing the marrow cavity of 6 to 10 week old mice with RPMI/10% FCS under sterile conditions. Murine spleen cells are harvested by physical passage through a fine metal screen under sterile conditions. One of three methods are used to deplete the mixed hematopoietic cell population of its stromal component. As a first alternative, the hematopoietic stem cell population from the blood sample will be enriched by magnetic immunobead purification using anti-CD34 antigen according to established techniques. As a second alternative, hematopoietic cells will be enriched by passage of the bone marrow or other blood sample over a sterile G-10 Sephadex or nylon wool column; hematopoietic progenitor cells are eluted while stromal, cells are retained. As a third alternative, hematopoietic cells will be enriched by flow cytometric sorting. The hematopoietic cells are washed once and the number of nucleated cells is counted using a hematocytometer after erythrocyte lysis with 0.3% acetic acid and trypan blue staining. Hematopoietic cells are introduced into the liquid co-cultures at a ratio of preferably 10 to 100 nucleated hematopoietic cells per stromal cell plated, more preferably 20 to 30 nucleated hematopoietic cells per stromal cell plated, most preferably 25 to 30 nucleated hematopoietic cells per stromal cell plated. Cells are cultured in a medium consisting of RPMI1640, pre-screened 10% fetal bovine serum, 10 to 200 units/ml of penicillin, 10 to 200 $\mu$g/ml of streptomycin, 0.5 to 2 mM L-glutamine, 10 to 100 $\mu$M 2-mercaptoethanol at 37° C. in 5% $CO_2$. One half of the medium in the co-cultures is replaced every 3 to 4 days. The number of non-adherent cells in the medium is determined by hematocytometer count and/or by flow cytometry. The surface antigen characteristics of the non-adherent cells are documented using routine antibody markers for the major hematopoietic cell lineages. These will include, but are not limited to, Mac-1, Thy 1, Ig Heavy chain, Ter-81 (erythroid marker). The number and character of the non-adherent cell population is determined over a period of up to 10 weeks. At the conclusion of the study, the cellular composition of the adherent cell layer is determined by flow cytometric or immunohistochemical methods. As an alternative approach, the hematopoietic studies are conducted in semi-solid cultures. Cells are prepared as described above but the hematopoietic progenitor cells are plated in the additional presence of 2.1% methylcellulose. Colony formation is assessed after a 7 to 14 day period for the presence of B lineage lymphoid cells as well as granulocytes, erythrocytes, macrophages, and monocytes using histologic, morphologic and immunologic criteria. Alternatively, co-cultures and/or semi-solid cultures are established as described above with the addition of interleukin 7 at concentrations to be determined by the practictioner which enhance the proliferation and maturation of B lineage lymphocytes. The techniques outlined above are used to assess the affect of this growth factor on the hematopoietic support function of the adipose tissue derived stromal cell.

Example 5

Establishment of Osteoclastogenic Co-Cultures with an Adipose Tissue-Derived Stromal Cells Layer in vitro Stromal cells are isolated from human subcutaneous adipose tissue according to methods described in "Methods and Compositions for the Differentiation of Human Preadipocytes into Adipocytes" Ser. No. 09/240,029, Filed Jan. 29, 1999. These cells are plated at a density of 500 to 20,000 cells per cm² in 24 well plates. Cells are cultured in a medium consisting of DMEM (high glucose), prescreened 10% fetal bovine serum, 10 to 200 units/ml of penicillin, 10 to 200 $\mu$g of streptomycin, 0.5 to 2 mM L-glutamine, 0.5 to 2 mM sodium pyruvate, 10 to 100 $\mu$M 2-mercaptoethanol at 37° C. in 5% $CO_2$. Three days after the stromal cultures are established, the medium is supplemented with either 10 to 100 nM 1,25 dihydroxy vitamin $D_3$ and or osteoprotegerin ligand at concentrations determined by the practitioner. Stromal cells are established in the cultures for 6 days prior to the introduction of hematopoietic progenitor cells into the co-culture system.

Hematopoietic progenitor cells are isolated from one of the following human tissues: bone marrow, umbilical vein/placental blood, peripheral blood, spleen. Alternatively, murine tissues are used. Murine bone marrow cells are harvested by flushing the marrow cavity of 6 to 10 week old mice with DMEM (high glucose)/10% FCS under sterile conditions. Murine spleen cells are harvested by physical passage through a fine metal screen under sterile conditions. One of three methods are used to deplete the mixed hematopoietic cell population of its stromal component. As a first alternative, the hematopoietic stem cell population from the blood sample will be enriched by magnetic immunobead purification using anti-CD34 antigen according to established techniques. As a second alternative, hematopoietic cells will be enriched by passage of the bone marrow or other blood sample over a sterile G-10 Sephadex or nylon wool column; hematopoietic progenitor cells are eluted while stromal cells are retained. As a third alternative, hematopoietic cells will be enriched by flow cytometric sorting based on surface protein characteristics. The hematopoietic cells are washed once and the number of nucleated cells is counted using a hematocytometer after erythrocyte lysis with 0.3% acetic acid and trypan blue staining. Hematopoietic cells are introduced into the liquid co-cultures at a ratio of preferably 10 to 100 nucleated hematopoietic cells per stromal cell plated, more preferably 20 to 30 nucleated hematopoietic cells per stromal cell plated, most preferably 25 to 30 nucleated hematopoietic cells per stromal cell plated. One half of the medium in the co-cultures is replaced every 3 to 4 days. Co-cultures are maintained in the presence of 1,25 dihydroxy vitamin $D_3$ or osteoprotegerin ligand continuously after the introduction of hematopoietic cells.

After a period of co-culture of 6 to 9 days, co-cultures are fixed with 0.5 ml 3.7% (vol:vol) formaldehyde in phosphate buffered saline for 5 minutes, dried for 30 seconds with acetone:ethanol (50:50, vol/vol), and stained for 10 minutes with 10 mM sodium tartrate, 40 mM sodium acetate (pH 5.0), 0.1 mg/ml naphthol AS-MS phosphate (Sigma N-5000), and 0.6 mg/ml fast red violet LB salt (Sigma F-3381). Stained cultures are rinsed in distilled water and stored under 50% glycerol/PBS. The number of tartrate resistant acid phosphatase positive cells per well is assessed under light microscopy based on the red staining of the cytoplasm. TRAP+ cells are, numerically counted and those with 1–2 nuclei are distinguished from those multinucleated cells with $\geq 3$ nuclei per cell. This assay demonstrates the ability of adipose tissue derived stromal cells to support the differentiation and proliferation of osteoclastogenic precursors in vitro. This culture procedure is able to expand and promote differentiation of osteoclasts. This has potential application to rare clinical conditions such as osteopetrosis characterized by brittle bones where patients fail to produce native osteoclasts. This In vitro method offers a means to expand an individual's own osteoclast progenitors and to promote their differentiation ex vivo. This cell population can be re-infused into the affected individual with potential short-term or long-term benefit. The non-invasive nature of the methodology and the potential to rely exclusively on autologous cells indicates that this procedure could be used repetitively in the treatment of an individual patient.

Example 6

Use of Adipose Tissue Derived Stromal Cell Supported Ex vivo Hematopoiesis as a Therapeutic Modality for Bone Marrow Transplant and Hematologically Compromised Patients The co-culture models outlined in Examples 1–4 have the potential to be used to facilitate the recovery of bone marrow function in patients' receiving high dose chemotherapy, high dose radiation treatment or any other therapeutic modality which compromises blood cell production and bone marrow function. In advance of any elective procedure, an individual can donate his or her own adipose tissue and blood cells for subsequent autologous transplantation. Prior to immunocompromising procedures, the individual's own blood cells and stromal co-cultures can be established and expanded. Following any immunocompromising procedure, the patients own blood cell/stromal cell co-culture can be re-infused into the patient according to standard transfusion methodologies. This can be done in the absence or presence of exogenous hematopoietic cytokines, either added to the co-cultures or given directly to the patient. This approach may accelerate the rate of blood cell production in the patient, reduce the need for cytokine therapies, and reduce the overall costs and risk of the chemotherapy or other immunocompromising procedure. With the, ex vivo nature of the procedure, it is possible to manipulate the stromal cells to enhance production of specific blood cell lineages. Stromal cells transiently expressing interleukin 7, for example, would facilitate the rapid expansion of B lineage lymphoid cells while stromal cells expressing erythropoietin would favor expansion of erythrocytes.

As outlined above, the approach is designed primarily for the treatment of nosocomial induced blood cell dyscrasias. However, large scale ex vivo production of autologous stromal/hematopoietic co-cultures is of potential value for elective and non-elective surgical procedures requiring transfusion intra-operatively and post-operatively. At present, the majority of patients requiring blood transfusion receive blood products donated by others. This presents risk to the recipient of transmission of unrecognized infectious disease from the donor. With the ability to develop blood cell production ex vivo, an individual can expand his/her hematopoietic cell population at a capacity which is no longer limited by the bone marrow cavity volume. Using cell factory tissue culture approaches with recirculating systems, continuous production of blood cells by an adipose tissue derived stromal cell/hematopoietic cell co-culture is feasible. This approach has the advantage of avoiding risks inherent in transfusion of blood from a donor to a recipient; these include the transmission of infectious diseases such as HIV, hepatitis, cytomegalovirus, Jacob/Creukzfeld disease, among others.

Example 7

Differentiation of Adipose Tissue Derived Stromal Cells into Skeletal Muscle Myoblasts Stromal cells are isolated from human subcutaneous adipose tissue according to methods described in "Methods and Compositions for the Differentiation of Human Preadipocytes into Adipocytes" Ser. No. 09/240,029, filed Jan. 29, 1999. These cells are plated at a density of 500 to 20,000 cells per $cm^2$ in 24 well plates. Cells are cultured in a medium consisting of DMEM (high glucose), prescreened 10% fetal bovine serum, 10 to 200 units/ml of penicillin, 10 to 200 µg of streptomycin, 0.5 to 2 mM L-glutamine, 0.5 to 2 mM sodium pyruvate, 10 to 100 µM 2-mercaptoethanol at 37° C. in 5% $CO_2$. Cells are exposed to 1 to 30 µM 5' azacytadine or 10 to 100 ng/ml of amphotericin for periods of 1 to 6 days to assure that cells throughout S phase are continuously exposed to these agents. Following this period, cultures are maintained in the culture medium without azacytadine or amphotericin supplements. Cultures are either continued at the established cell density or sub-cloned by limit dilution methods to select for cell clones capable of expressing characteristic markers of skeletal muscle myoblasts. These cells are selected based on morphologic criteria, specifically, the ability to form multinucleated myotubules in culture; biochemical criteria, specifically, the expression of myosin heavy and light chain kinase, skeletal muscle actin and myosin and the expression of myogenic transcription factors, myoD and/or myogenin.

Example 8

Application of Skeletal Muscle Myoblasts Differentiated from Adipose Tissue-Derived Stromal Cell The cells skeletal muscle myoblasts developed in Example 6 can be used for tissue engineering purposes in the treatment of myodystrophies, muscle atrophy, and physical loss of skeletal muscle secondary to surgical procedures for the treatment of cancer or trauma. The ex vivo development of a proliferating population of myoblasts from adipose tissue can be used to supplement and repair skeletal muscle mass in afflicted individuals. Myoblasts can be cultured in biodegradable matrices composed of poly-lactic, polyglycolic, collagen or other materials to form muscle strands. These can then be implanted to an afflicted site and tethered by suture to existing muscle, tendon or bone. Alternatively, ex vivo expanded myoblasts can be genetically engineered by viral transduction, plasmid transfection, or other means to express novel genes. These cells can be injected directly into existing muscle sites where these novel gene products will now be expressed. This approach has direct application to muscular dystrophy, where patients suffer secondary to a mutation in an important skeletal muscle gene. Likewise, the engineered stromal cells can convert the muscle into a production site for a deficient circulating protein. For example, adipose tissue derived stromal cells expressing lipoprotein lipase can be used to treat the many patients with mutations in their native lipoprotein lipase gene who are at increased risk of severe cardiovascular disease.

Example 9

Differentiation and Expansion of Smooth Muscle Myoblasts from Adipose Tissue Derived Stromal Cells Ex vivo Stromal cells are isolated from human subcutaneous adipose tissue according to methods described in "Methods and Compositions for the Differentiation of Human Preadipocytes into Adipocytes" Ser. No. 09/240,029, filed Jan. 29, 1999. These cells are plated at a density of 500 to 20,000 cells per $cm^2$ in 24 well plates. Cells are cultured in a medium consisting of DMEM (high glucose), prescreened 10% fetal bovine serum, 10 to 200 units/ml of penicillin, 10 to 200 µg of streptomycin, 0.5 to 2 mM L-glutamine, 0.5 to 2 mM sodium pyruvate, at 37° C. in 5% $CO_2$. Cultures are supplemented with transforming growth factor β and/or fibroblast growth factor at concentrations determined by the practitioner but not to exceed 40 ng/. Cells are maintained in culture as a monolayer or in a 3-dimensional lattice composed of collagen type I or other biodegradable material (alginate, synthetic polymer or other). Cells are characterized based on morphologic, biochemical, and functional criteria for smooth muscle myoblast differentiation; these include, but are not limited to, expression of smooth muscle actin, fibronectin, laminin, and other extracellular matrix proteins, the ability to generate a tensile force as measured by a pressure transducer, and to organize along a line of force in a 3 dimensional lattice.

Example 10

Application of Smooth Muscle Myoblasts Differentiated from Adipose Tissue-Derived Stromal Cells Ex vivo The smooth muscle myoblasts described under Example 8 can be used to treat conditions where smooth muscle function is compromised. For example, over 1000 neonates each year suffer from bladder wall abnormalities. The severity of this disorder is variable but it can be devastating and requires expensive surgical procedures to accomplish an acceptable repair and an approach to normal function. In many cases, the bladder size is too small or the bladder wall is incompletely formed, necessitating the implantation of prosthetic materials as a bladder wall replacement. Methods under investigation include the use of swine intestinal submucosa as a replacement material for the bladder wall. One issue is whether or not the surgically implanted bladder wall will achieve the appropriate physical and mechanical characteristics associated with stretching and retraction. Much of this is mediated by functional smooth muscle cells. Current methods implant the SIS material without preimplantation of any smooth muscle cells ex vivo. Surgeons rely on the recruitment of fibroblasts and myofibroblasts from adjacent tissues, including the omental adipose tissue. With the availablity of adipose tissue derived stromal cells capable of smooth muscle myoblast differentiation, it is possible to pre-incubate S1S material with these cells ex vivo. The introduction of these cells prior to the surgical repair of the bladder wall is expected to accelerate and improve the attainment of appropriate bladder tone. This approach has broad application to all elastic soft tissue organs which rely on smooth muscle cells. These include, but are not limited to, the small intestine, large intestine, vagina, urethra, and venous blood vessels. The adipose tissue derived stromal cells have potential application to the surgical repair of defects in any of these organs.

All publications mentioned in the specification are indicative of the level of those skilled in the art to which this invention pertains. Publications are herein incorporated by reference to the same extent as if each individual publication was specifically and individually indicated to be incorporated by reference.

Although the foregoing invention has been described in some detail by way of illustration and example for purposes of clarity and understanding, it will be obvious that certain changes and modifications may be practiced within the scope of the appended claims.

What is claimed is:

1. A non-naturally-occurring mixture of cells comprising an isolated extramedullary adipose tissue-derived stromal cell and a non-adipose derived cell capable of forming a blood cell.

2. The mixture of cells of claim 1, wherein the non-adipose-derived cell capable of forming a blood cell is selected from the group consisting of a hematopoietic stem cell and a hematopoietic progenitor cell.

3. The mixture of cells of claim 1, wherein the non-adipose-derived cells capable of forming a blood cell is a hematopoietic stem cell.

4. The mixture of cells of claim 1, wherein the non-adipose-derived cell capable of forming a blood cell is selected from the group consisting of a hematopoietic stem cell and a myeloid cell.

5. The mixture of cells of claim 1, wherein the non-adipose-derived cell capable of forming a blood cell is selected from the group consisting of a hematopoietic stem cell and a lymphoid cell.

6. The mixture of cells of claim 1, wherein the non-adipose-derived cell capable of forming a blood cell is selected from the group consisting of a hematopoietic stem cell and an erythroid cell.

7. The mixture of cells of claim 1, wherein the non-adipose-derived cell capable of forming a blood cell is selected from the group consisting of a hematopoietic stem cell and a megakaryocyte cell.

8. The mixture of cells of claim 1, wherein the non-adipose-derived cell capable of forming a blood cell is selected from the group consisting of a hematopoietic stem cell and an osteoclast.

9. The mixture of cells of claim 1, wherein the formed blood cell is a hematopoietic progenitor cell.

10. The mixture of cells of claim 1, wherein the formed blood cell is a hematopoietic stem cell.

11. The mixture of cells of claim 1, wherein the formed blood cell is a myeloid cell.

12. The mixture of cells of claim 1, wherein the formed blood cell is a lymphoid cell.

13. The mixture of cells of claim 1, wherein the formed blood cell is an erythroid cell.

14. The mixture of cells of claim 1, wherein the formed blood cell is a megakaryocyte cell.

15. The mixture of cells of claim 1, wherein the formed blood cell is an osteoclast.

16. The mixture of cells of claim 1, wherein the non-adipose-derived cell capable of forming a blood cell is selected from the group consisting of a hematopoietic progenitor cell, hematopoietic stem cell, myeloid cell, lymphoid cell, erythroid cell, megakaryocyte cell, and osteoclast.

17. The mixture of cells of claim 1, wherein the non-adipose-derived cell capable of forming a blood cell is selected from the group consisting of a hematopoietic a progenitor cell, hematopoietic stem cell and myeloid cell.

18. The mixture of cells of claim 1, wherein the non-adipose-derived cell capable of forming a blood cell is selected from the groups consisting of a hematopoietic stem cell, myeloid cell and lymphoid cell.

19. The mixture of cells of claim 1, wherein the non-adipose-derived cell capable of forming a blood cell is selected from the group consisting of a hematopoietic stem cell, erythroid cell and megakaryocyte cell.

20. The mixture of cells of claim 1, wherein the non-adipose-derived cell capable of forming a blood cell is selected from the group consisting of a hematopoietic stem cell, lymphoid cell and osteoclast.

21. The mixture of cells of claim 1, wherein the non-adipose-derived cell capable of forming a blood cell is selected from the group consisting of a hematopoietic stem cell, lymphoid cell and a megakaryocyte cell.

22. The mixture of cells of claim 1, wherein the non-adipose-derived cell capable of forming a blood cell is selected from the group consisting of a hematopoietic stem cell, erythroid cell and lymphoid cell.

23. The mixture of cells of claim 1, wherein the non-adipose-derived cell capable of forming a blood cell is selected from the group consisting of a hematopoietic stem cell, erythroid cell and an osteoclast.

24. The mixture of cells of claim 1, wherein the non-adipose-derived cell capable of forming a blood cell is selected from the group consisting of a hematopoietic stem cell, megakaryocyte cell and an osteoclast.

25. A mixture of cells comprising an isolated extramedullary adipose tissue-derived stromal cell and a non-adipose derived cell capable of forming a blood cell.

26. A mixture of cells comprising an isolated human extramedullary adipose tissue-derived stromal cell and a non-adipose derived cell capable of forming a blood cell.

27. A mixture of cells comprising an isolated adult human extramedullary adipose tissue-derived stromal cell and a non-adipose derived cell capable of forming a blood cell.

28. A mixture of cells comprising an isolated adult human extramedullary adipose tissue-derived stromal cell and a non-adipose derived human cell capable of forming a blood cell.

* * * * *